United States Patent [19]

Matsushita et al.

[11] Patent Number: 4,794,798
[45] Date of Patent: Jan. 3, 1989

[54] DEVICE FOR MEASURING YOUNG'S MODULUS AND INTERNAL FRICTION OF SPECIMEN

[75] Inventors: Ken-ichi Matsushita; Taira Okamoto, both of Osaka; Masahiko Shimada, Miyagi; Hisao Takeuchi, Hyogo, all of Japan

[73] Assignee: Sumitomo Electric Industried Limited, Osaka, Japan

[21] Appl. No.: 33,187

[22] Filed: Apr. 2, 1987

[51] Int. Cl.[4] ............................................. G01N 3/00
[52] U.S. Cl. ......................................... 73/789; 73/849
[58] Field of Search ................ 73/789, 849, 811, 812, 73/579, 662; 374/47, 52; 324/452

[56] References Cited

U.S. PATENT DOCUMENTS

| 2,404,584 | 7/1946 | Liska et al. | 374/52 |
| 3,015,947 | 1/1962 | Kadel | 374/52 |

Primary Examiner—Jerry W. Myracle
Attorney, Agent, or Firm—Kerkam, Stowell, Kondracki & Clarke

[57] ABSTRACT

Herein disclosed is a transverse resonance measurement device for measuring the Young's modulus and/or internal friction of the plate specimen of a material over a wide temperature range even if the material is nonconductive, e.g., ceramics, wood or plastics. Platinum paste is applied to one side of a plate specimen to be measured, and is baked into a platinum electrode.

16 Claims, 2 Drawing Sheets

DEVICE FOR MEASURING YOUNG'S MODULUS AND INTERNAL FRICTION OF SPECIMEN

BACKGROUND OF THE INVENTION

1. Field of the Invention

The present invention relates to a technique for measuring the Young's modulus and internal friction of a specimen and, more particularly, to a transverse resonance measurement device for measuring the Young's modulus and internal friction of a specimen of a ceramic, metallic or wooden material or the like over a wide temperature range (e.g. −250° to 1,500° C.) even if the material is not conductive.

2. Description of related art

In recent years, researches and developments of ceramic materials which are very strong even at a high temperature are highlighted. However, few reports are presented on the Young's moduli and internal friction of such materials at high temperatures.

Before entering into the detailed description of the present invention, brief review will be made in the following on one of the existing Young's modulus measurements, in which a specimen 11 is suspended in a horizontal position from two platinum wires 12 so that it may resonate transversely, as shown in FIG. 1. The specimen 11 is confined in and heated by a tubular oven 13. For the transverse resonance, the specimen 11 is shook by a shaker 14 through one platinum wire 12. The transverse vibrations of the specimen 11 are detected by means of a detector 15 to measure the Young's modulus.

According to this method, however, the suspending platinum wires will resonate making it difficult to determine the resonant frequency of the specimen. Because of the considerable thickness of the wires, moreover, much of their vibration energy is lost. Still moreover, the suspension points provide the nodes of the vibration to drop the vibration efficiency so that serious errors are caused in the measurements of the Young's modulus (and the internal friction). According to this method, furthermore, the atmosphere is difficult to regulate because the oven 13 is formed in its top with holes 16 for leading out the platinum wires 12.

SUMMARY OF THE INVENTION

It is, therefore, an object of the present invention to provide a transverse resonance measurement device for measuring the Young's modulus and internal friction of a specimen, which device solves the various problems of the prior art by efficiently resonating the specimen.

According to a major aspect of the present invention, there is provided a transverse resonance measurement device for measuring the Young's modulus and/or internal friction of a plate specimen of a material over a wide temperature range even if the material is nonconductive, which device comprises:

a vessel having a chamber for confining an inert atmosphere therein;

temperature regulating means for regulating the temperature of the inert atmosphere in the chamber of vessel;

a first electrode applied to one side of the specimen;

a refractory jig placed in the chamber of the vessel and having two end ridges for supporting opposite end portions of a first electrode on their tops;

two conductive wires fitted on the tops of the two end ridges of the jig, and adapted to be in contact with the first electrode when the specimen is supported by the jig;

a second electrode extended on the center portion of the jig between the two end ridges thereof;

means for applying an alternating voltage between one of the wires and the second electrode to resonate the specimen relative to the jig; and means for detecting the Young's modulus and/or internal friction of the specimen while the latter is being resonated.

The present invention is characterized by applying platinum paste to one side of a plate specimen to be measured, and baking it into a platinum electrode. This makes is possible to measure even nonconductive materials such as ceramics, wood or plastics.

BRIEF DESCRIPTION OF THE DRAWINGS

The above and other objects, features and advantages of the present invention will become apparent from the following description taken with reference to the accompanying drawings, in which.

DESCRIPTION OF THE PREFERRED EMBODIMENT

Figure 1:
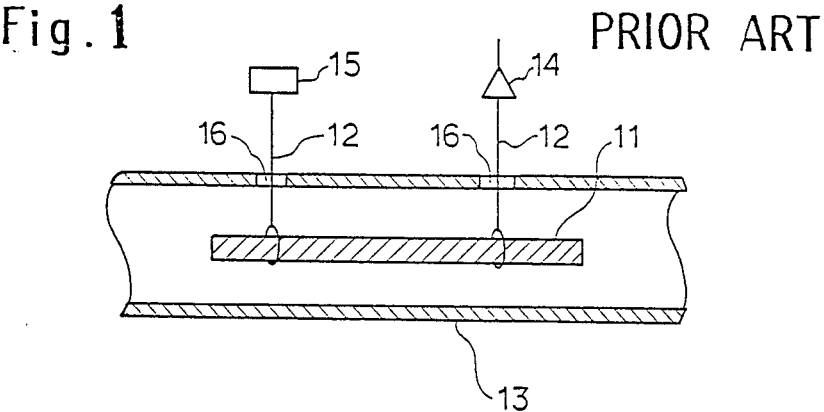
FIG. 1 is a schematic view showing the measuring method of the prior art.
Figure 2:
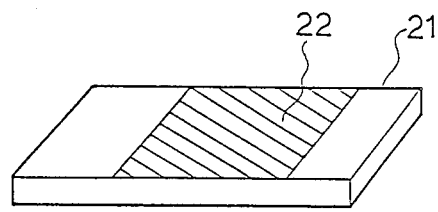
FIG. 2 is a perspective view showing a plate specimen to be measured by a transverse resonance measurement device of the present invention.
Figure 3:
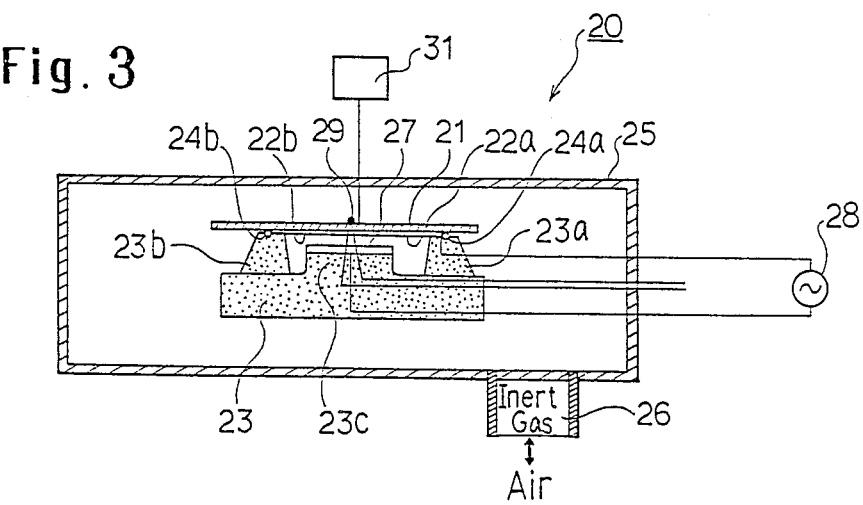
FIG. 3 is a front section showing the transverse resonance measurement device according to the present invention.

With reference to FIG. 2, there is shown a plate specimen 21 which is to be measured by the transverse resonance device which is generally designated at 20 in FIG. 3. A platinum film-like electrode 22 is applied in the form of platinum paste to one side of the specimen 21. The resonance device 20 has an electrically insulative jig 23 having two end ridges 23a and 23b so that the platinum electrode 22 is placed on the tops of the ridges 23a and 23b. This electrode 22 can be made of other heat-resistant and electrically conductive materials as Mo, C and the like. Platinum wires 24a and 24b are fixed on the ridges 23a and 23b of the jig 23, respectively. These wires 24a and 24b can be made of Mo, Ta, Ni and other heat-resistant and electrically conductive metals. One of these wires 24a is connected to one terminal of an AC source, as explained hereinafter, and the other wire 24b is grounded.

Figure 4:
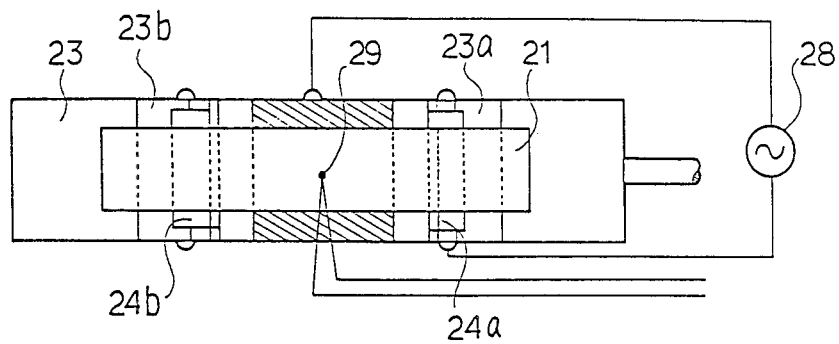
FIG. 4 is a top plan view showing the specimen supported on a jig in accordance with the present invention.

Thus, the specimen 21 prepared as mentioned above is put on the jig 23 in such a manner that the electrode 22 of the specimen 21 contacts at its one end region 22a with one platinum wire 24a and at its other end region 22b with the platinum wire 24b, as shown in FIG. 3. As a result, the electrode 22 of the specimen 21 is applied through the wire 24a with an AC voltage and grounded through the wire 24b. The top plan view showing how the specimen 21 is placed on the jig 23, is presented in FIG. 4.

Further, the jig 23 has a projected land portion 23c formed between the pair of ridges 23a and 23b. This projected land 23c has a flat surface formed with a sheet-like drive electrode 27, which is opposite to and separate from the electrode 22 of the specimen 21 when the specimen 21 is put on the ridges 23a and 23b. Namely, a capacitor is formed between the electrode 22 of the specimen 21 and the drive electrode 27 of the jig 23. The drive electrode 27 is formed of a heat-resistant and electrically conductive metal such as Mo, Pt and the like. Particularly, if a very high heat-resistance is required, the jig 23 and the electrode 27 are integrally formed of an electrically conductive heat-resistant ceramics such as SiC. In this case, the wires 24a and 24b are provided through an insulative material on the top of the ridges 23a and 23b.

The specimen 21 is put into a vessel 25 which is formed with a port 26 for evacuating the vessel 25 or introducing an atmospheric inert gas into the vessel 25, as shown in FIG. 3. An alternating current is applied between the drive electrode 27 and the platinum electrode 22 on the side of the specimen 21 by connecting a pair of terminals of an alternating voltage source 28 to the wire 24a on the ridge 23a and the drive electrode 27, respectively. As a result, an alternating force acts between the electrodes 22 and 27, so that the specimen 21 is vibrated because the electrode 22 is firmly bonded to the specimen 21. Since, in this configuration, the electrodes 22 and 27 are positioned at the center of the specimen 21, the vibrational amplitude is substantially doubled to efficiently exploit the vibrations.

The temperature range for the measurements can be extended to as high as 1,500° C. by externally heating the chamber of the vessel 25 to maintain it at a predetermined temperature. The lower limit of the temperature for the measurements can also be as low as −250° C. by cooling the vessel chamber with liquid helium. This temperature can be measured by means of a thermocouple 29 mounted in the jig 23. On the other hand, the atmosphere for the measurements can be prepared by evacuating the vessel chamber or by filling the same with a non-oxidizing or inert gas such as Ar or $N_2$.

Thus, the Young's modulus and/or internal friction of the specimen 21 can be measured by means of a detector 31. For example, the alternating voltage to be applied may be 500 to 1,000 V, and the resonant frequency may be 50 Hz to 50 KHz.

The jig 23 is made of $Al_2O_3$, BN or SiC so that it may withstand the high temperature. The specimen 21 may be sized within a range from $1 \times 5 \times 20$ mm to $3 \times 15 \times 150$ mm, but this size can be changed depending the jig size.

EXAMPLE

Figure 5:
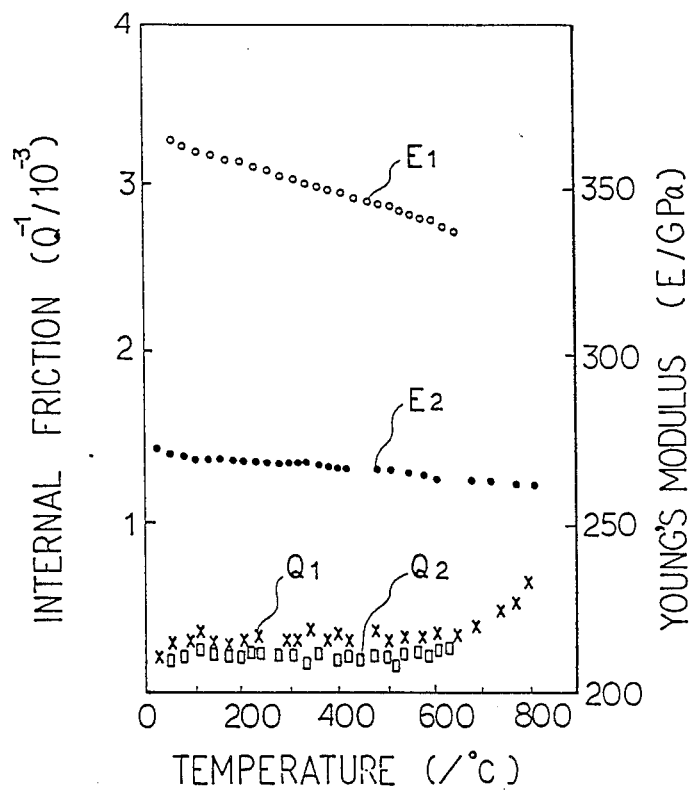
FIG. 5 is a graph plotting the Young's moduli and internal frictions measured by the device of the present invention to present their temperature dependencies.

Two specimens were made of sintered materials of $Al_2O_3$ and $Si_3N_4$ and worked to have a common size of $1.5 \times 10 \times 60$ mm. Platinum paste was applied to one side of each specimen and baked. The Young's moduli and internal friction of the specimens thus prepared were measured at the room temperature and at various temperatures up to 800° C. by means of the device shown in FIG. 3. The measurement results are plotted in FIG. 5, in which blank circles (E1) and solid circles (E2) show the Young's moduli of $Al_2O_3$ and $Si_3N_4$, respectively, whereas blank squares (Q2) and solid squares (Q2) show the internal frictions of the same, respectively.

The invention has thus been shown and described with reference to specific embodiments. However, it should be noted that the invention is in no way limited to the details of the illustrated structures but changes and modifications may be made within the scope of the appended claims.

What is claimed is:

1. A transverse resonance measurement device for measuring the Young's modulus and/or internal friction of a plate specimen of a material over a wide temperature range even if the material is inconductive, comprising:
    a vessel having a chamber for confining an inert atmosphere therein;
    temperature regulating means for regulating the temperature of the inert atmosphere in the chamber of said vessel;
    a first electrode applied to one side of said specimen;
    a refractory jig placed in the chamber of said vessel and having two end ridges for supporting opposite end portions of said electrode on their tops;
    two conductive wires fitted on the tops of the two end ridges of said jig, and adapted to be in contact with the first electrode when said specimen is supported by said jig;
    a second electrode extended on the center of said jig between said two end ridges;
    means for applying an alternating voltage between one of said wires and said second electrode to resonate said specimen relative to said jig; and
    a detector for detecting the Young's modulus and/or internal friction of said specimen while the latter is being resonated.

2. A traverse resonance measurement device according to claim 1, wherein said temperature regulating means includes:
    a thermocouple mounted in said jig for measuring the temperature of said inert atmosphere so as to make it possible to control said inert atmosphere at a predetermined temperature in accordance with the temperature measured by said thermocouple.

3. A transverse resonance measurement device according to claim 1, further comprising an atmosphere controller including a port formed in said vessel for evacuating the chamber of the same or filling said chamber with an inert gas.

4. A transverse resonance measurement device according to claim 1, wherein said first electrode is made of baked platinum paste.

5. A transverse resonance measurement device according to claim 1, wherein said jig is made of $Al_2O_3$, BN or SiC.

6. A transverse resonance measurement device according to claim 1, wherein said specimen has a size from $1 \times 5 \times 10$ mm to $3 \times 15 \times 150$ mm.

7. A transverse resonance measurement device for measuring the Young's modulus and/or internal friction of a plate specimen of a non-conductive material over a wide temperature range, said specimen having a conductive coating firmly bonded on one surface thereof, the device comprising:
    a refractory jig having two end ridges for supporting opposite end portions of said conductive coating of said specimen on their tops;
    one electrode formed fitted on the top of at least one of the two end ridges of said jig, and adapted to be in electrical contact with said conductive coating of the said specimen when said specimen is supported by said jig;
    a second electrode formed on a center portion of said jig between said two end ridges;

means for applying an alternating voltage between said first and said second electrodes to vibrate said specimen relative to said jig; and means for detecting the Young's modulus and/or internal friction of said specimen while the latter is being resonated.

8. A transverse resonance measurement device according to claim 7, wherein said jig is located in a vessel which can be filled with an inert gas or evacuated, said vessel including a thermocouple mounted in said jig for measuring the temperature of said inert atmosphere and a temperature controller for maintaining said inert atmosphere at a predetermined temperature in accordance with the temperature measured by said thermocouple.

9. A transverse resonance measurement device according to claim 8, wherein an atmosphere controller includes a port formed in said vessel for evacuating the chamber of the same or filling said chamber with an inert gas.

10. A transverse resonance measurement device according to claim 7, wherein said coating of said specimen is made of backed platinum paste.

11. A transverse resonance measurement device according to claim 7, wherein said jig is made of $Al_2O_3$, BN or SiC.

12. A transverse resonance measurement device according to claim 7, wherein said specimen has a size from $1 \times 5 \times 10$ mm to $3 \times 15 \times 150$ mm.

13. A transverse resonance measurement device according to claim 7 wherein said coating of said specimen and said first and second electrodes are made of heat-resistant and electrically conductive material.

14. A transverse resonance measurement device according to claim 7 wherein said first electrode is formed of a material selected from the group consisting of Pt, Mo, To and Ni.

15. A transverse resonance measurement device according to claim 7 wherein said second electrode is formed of a material selected from the group consisting of Pt and Mo.

16. A transverse resonance measurement device according to claim 7 wherein said coating provided on the specimen is formed of a material selected from the group consisting of Pt, Mo and C.

* * * * *

UNITED STATES PATENT AND TRADEMARK OFFICE
CERTIFICATE OF CORRECTION

PATENT NO. : 4,794,798

DATED : January 3, 1989

INVENTOR(S) : Matsushita et al

It is certified that error appears in the above-identified patent and that said Letters Patent is hereby corrected as shown below:

Title page:

[73] Assignee: Sumitomo Electric Industries Ltd., Osaka, Japan and President Of Osaka University, Osaka, Japan Signed and Sealed this Thirtieth Day of May, 1989

Attest:

DONALD J. QUIGG

Attesting Officer

Commissioner of Patents and Trademarks